US010952691B2

(12) United States Patent
Cox

(10) Patent No.: US 10,952,691 B2
(45) Date of Patent: Mar. 23, 2021

(54) SCANNING DIGITAL FLUOROSCOPE COMPRISING MULTIPLE RADIOGRAPHIC IMAGE DETECTORS ARRANGED AS SPOKES EXTENDING RADIALLY OUTWARDLY FROM A CENTRAL ROTATIONAL POINT ON A ROTATIONAL PLATE

(71) Applicant: PRINCIPLE IMAGING CORPORATION, West Yellowstone, MT (US)

(72) Inventor: John D. Cox, Gainesville, FL (US)

(73) Assignee: PRINCIPLE IMAGING CORPORATION, West Yellowstone, MT (US)

( * ) Notice: Subject to any disclaimer, the term of this patent is extended or adjusted under 35 U.S.C. 154(b) by 573 days.

(21) Appl. No.: 15/617,959

(22) Filed: Jun. 8, 2017

(65) Prior Publication Data

US 2017/0354391 A1 Dec. 14, 2017

Related U.S. Application Data

(60) Provisional application No. 62/348,676, filed on Jun. 10, 2016.

(51) Int. Cl.
*A61B 6/00* (2006.01)
*A61B 6/06* (2006.01)

(52) U.S. Cl.
CPC ............... *A61B 6/487* (2013.01); *A61B 6/06* (2013.01); *A61B 6/40* (2013.01); *A61B 6/4085* (2013.01); *A61B 6/42* (2013.01); *A61B 6/4208* (2013.01); *A61B 6/4233* (2013.01); *A61B 6/44* (2013.01); *A61B 6/4429* (2013.01); *A61B 6/4435* (2013.01); *A61B 6/4441* (2013.01); *A61B 6/486* (2013.01); *A61B 6/508* (2013.01); *A61B 6/4078* (2013.01)

(58) Field of Classification Search
CPC ....... A61B 6/06; A61B 6/4078; A61B 6/4085; A61B 6/42; A61B 6/4208; A61B 6/4291; A61B 6/44; A61B 6/4435; A61B 6/4441; A61B 6/486; A61B 6/487; A61B 6/508; A61B 6/40; A61B 6/4233; A61B 6/4429; A61B 6/4452
USPC .......... 378/42, 62, 98.8, 147, 149, 154, 155, 378/189, 190, 196–198
See application file for complete search history.

(56) References Cited

U.S. PATENT DOCUMENTS 4,398,302 A * 8/1983 Pfeiler ..................... A61B 6/02
378/146
5,282,254 A * 1/1994 Chiu ......................... A61B 6/06
378/159

(Continued)

*Primary Examiner* — Allen C. Ho
(74) *Attorney, Agent, or Firm* — Rimon Law

(57) ABSTRACT

A system for taking fluoroscopic images of large animals having a rotatable plate with a plurality of detectors disposed on the rotatable plate, wherein the plurality of detectors are arranged as spokes extending radially outwardly from a central rotational point on the rotatable plate with collimators disposed on the side edges of the spokes. A drive assembly rotates the rotatable plate about an axis extending through the central rotational point at a speed such that the duration of successive image frames corresponds to the time taken for each spoke of detectors to move to the position of an adjacent spoke of detectors.

17 Claims, 3 Drawing Sheets

(56) References Cited

U.S. PATENT DOCUMENTS

| | | | | |
|---|---|---|---|---|
| 5,369,678 A * | 11/1994 | Chiu | ............... | A61B 6/06 378/152 |
| 6,067,342 A * | 5/2000 | Gordon | ............... | G01N 23/046 378/15 |
| 6,167,115 A * | 12/2000 | Inoue | ............... | G21K 1/025 378/154 |
| 6,181,773 B1 * | 1/2001 | Lee | ............... | G21K 1/025 378/154 |
| 6,778,632 B2 * | 8/2004 | Hoheisel | ............... | G21K 1/025 378/98.8 |
| 7,236,560 B2 * | 6/2007 | Malamud | ............... | A61B 6/032 250/505.1 |
| 7,340,032 B2 * | 3/2008 | Besson | ............... | A61B 6/025 250/370.1 |
| 7,342,993 B2 * | 3/2008 | Besson | ............... | A61B 6/025 250/370.1 |
| 7,366,279 B2 * | 4/2008 | Edic | ............... | A61B 6/032 378/150 |
| 7,539,284 B2 * | 5/2009 | Besson | ............... | A61B 6/032 378/147 |
| 8,249,216 B2 * | 8/2012 | Urushiya | ............... | A61B 6/12 378/92 |
| 8,483,362 B2 * | 7/2013 | Freund | ............... | G21K 1/025 378/147 |
| 8,873,703 B2 * | 10/2014 | Ruimi | ............... | A61B 6/032 378/7 |
| 9,161,727 B2 * | 10/2015 | Jenkins | ............... | G21K 1/04 |
| 9,263,160 B2 * | 2/2016 | Kang | ............... | G21K 1/025 |
| 9,320,476 B2 * | 4/2016 | Iso | ............... | A61B 6/03 |
| 9,782,138 B2 * | 10/2017 | Koehler | ............... | A61B 6/032 |
| 10,136,870 B2 * | 11/2018 | Ray | ............... | A61B 6/508 |
| 10,136,871 B2 * | 11/2018 | Yorkston | ............... | A61B 6/508 |

* cited by examiner

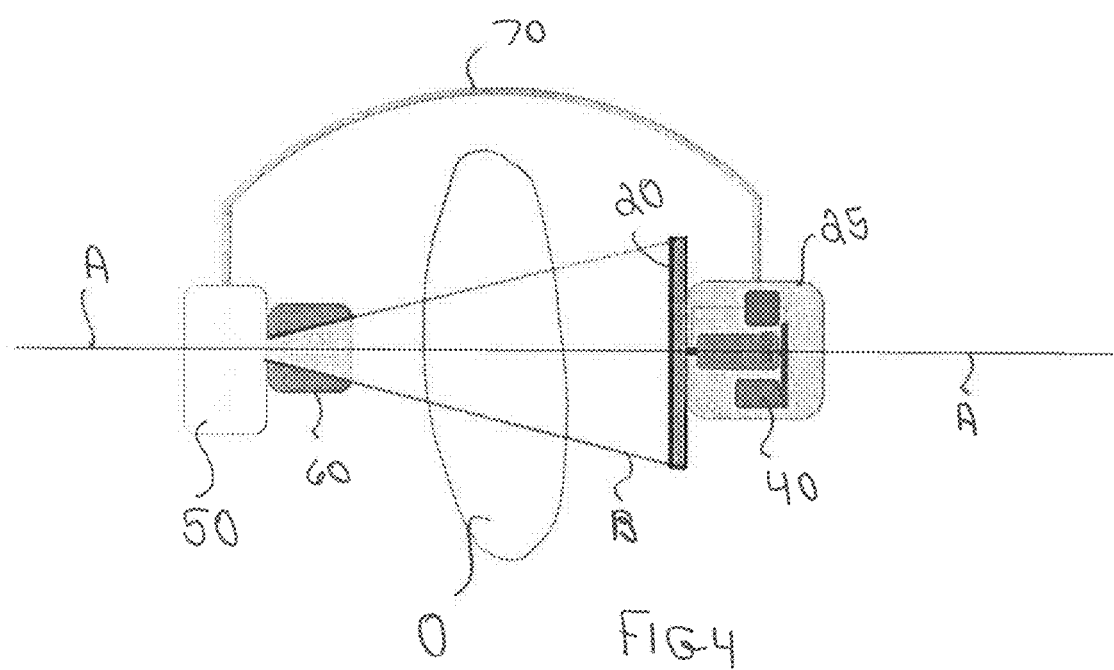

SCANNING DIGITAL FLUOROSCOPE COMPRISING MULTIPLE RADIOGRAPHIC IMAGE DETECTORS ARRANGED AS SPOKES EXTENDING RADIALLY OUTWARDLY FROM A CENTRAL ROTATIONAL POINT ON A ROTATIONAL PLATE

RELATED APPLICATION

The present application claims priority to U.S. Provisional Patent Application Ser. No. 62/348,676, of same title, filed Jun. 10, 2016, the entire disclosure of which is incorporated herein by reference in its entirety for all purposes.

TECHNICAL FIELD

The present system relates to fluoroscopic imaging in general and to veterinary applications of fluoroscopic imaging in particular. The present system also relates to serial radiography, and thereby encompasses all forms of dynamic radiography.

BACKGROUND OF THE INVENTION

Fluoroscopy is the practice of taking real time "live" X-ray images. This is done by capturing and displaying X-ray images at a high or low frame rate (e.g.: typically 2-30 frames per second). In operation, the fluoroscope uses an X-ray generator which sends an X-ray beam towards a detector array. The state of the art in fluoroscopy has until recently been based on the use of image intensifiers and, more recently, flat panel detectors. The use of either image intensifiers or flat-panel X-ray detectors employs projection radiography where the entire surface of the detector is illuminated by either a constant or pulsed beam of X-rays. Special X-ray tubes and generators are used in fluoroscopy to produce long X-ray exposures at relatively low X-ray exposure dosage (as compared with static radiography). As described herein, an X-ray generator encompasses any device that generates X-rays, for example X-ray tubes in particular.

Unfortunately, a common problem with conventional fluoroscopy is "X-ray scatter" in which the X-rays deflect off of the object being imaged. This has the result of introducing off-axis radiation scattered into the detector producing a fogging effect that degrades image quality. Traditional solutions to X-ray scatter include using anti-scatter grids. Unfortunately, as the object being scanned gets larger, the problem of the images becoming foggy increases as well (due to additional X-ray scatter within the larger object). This problem is particularly acute in large animal veterinary fluoroscopy.

As will be shown, the present system provides a novel mechanical solution to the current problem of X-ray scattering, thereby enabling an operator to obtain clear image scans of large animals.

SUMMARY OF THE INVENTION

The present system provides a mechanical solution to the problem of X-ray scatter, enabling an operator to obtain clear image scans of large objects. As such, the present system is particularly well suited to equine and large animal veterinary fluoroscopy.

In preferred aspects, the imaging system comprises: (a) a rotatable plate; (b) one or more linear detectors disposed on the rotatable plate, wherein the detector(s) are arranged as spoke(s) extending radially outwardly from a central rotational point on the rotatable plate; and (c) a drive assembly configured to rotate the rotatable plate about an axis extending through the central rotational point. Collimators may also be provided on the side edges of the spokes to prevent X-ray scattering from exposing the detectors. A C-arm may be provided to connect the drive to an X-ray generator, with the X-ray generator positioned to emit an X-ray beam across the surface of the rotatable plate.

In optional preferred aspects, the detectors are arranged as 8 spokes, positioned at 45 degree angles to one another, and the center of the X-ray beam is collinear with the axis extending through the focal spot of the X-ray generator and the central rotational point of the rotatable plate. In another preferred embodiment, only one detector spoke is used.

The present system also provides a method of obtaining a fluoroscopic image, comprising: (a) positioning an object between an X-ray generator and a rotatable plate having a plurality of detectors thereon, wherein the detectors are arranged as one or more spokes extending radially outwardly from a central rotational point on the rotatable plate; (b) directing an X-ray beam through the object towards the detectors on the rotatable plate; while (c) rotating the rotatable plate, such that the detector(s) on the rotatable plate obtain a swept image of portions of the object between the adjacent spokes of detectors.

In preferred aspects, directing an X-ray beam through the object towards the detectors on the rotatable plate comprises taking successive image frames, with the duration of each image frame corresponding to the time taken for each spoke of detectors to move to the position of an adjacent spoke of detectors. As such, the rotatable plate is rotated at a speed such that the duration of successive image frames corresponds to the time taken for each spoke of detectors to move to the position of an adjacent spoke of detectors.

An important advantage of the present mechanical system is that is reduces the problem of off-axis beam scattering within the object, thereby providing much clearer fluoroscopic images.

BRIEF DESCRIPTION OF THE DRAWINGS

FIG. 4 is a top plan view of the present system in operation.

DETAILED DESCRIPTION OF THE DRAWINGS

Figure 1:
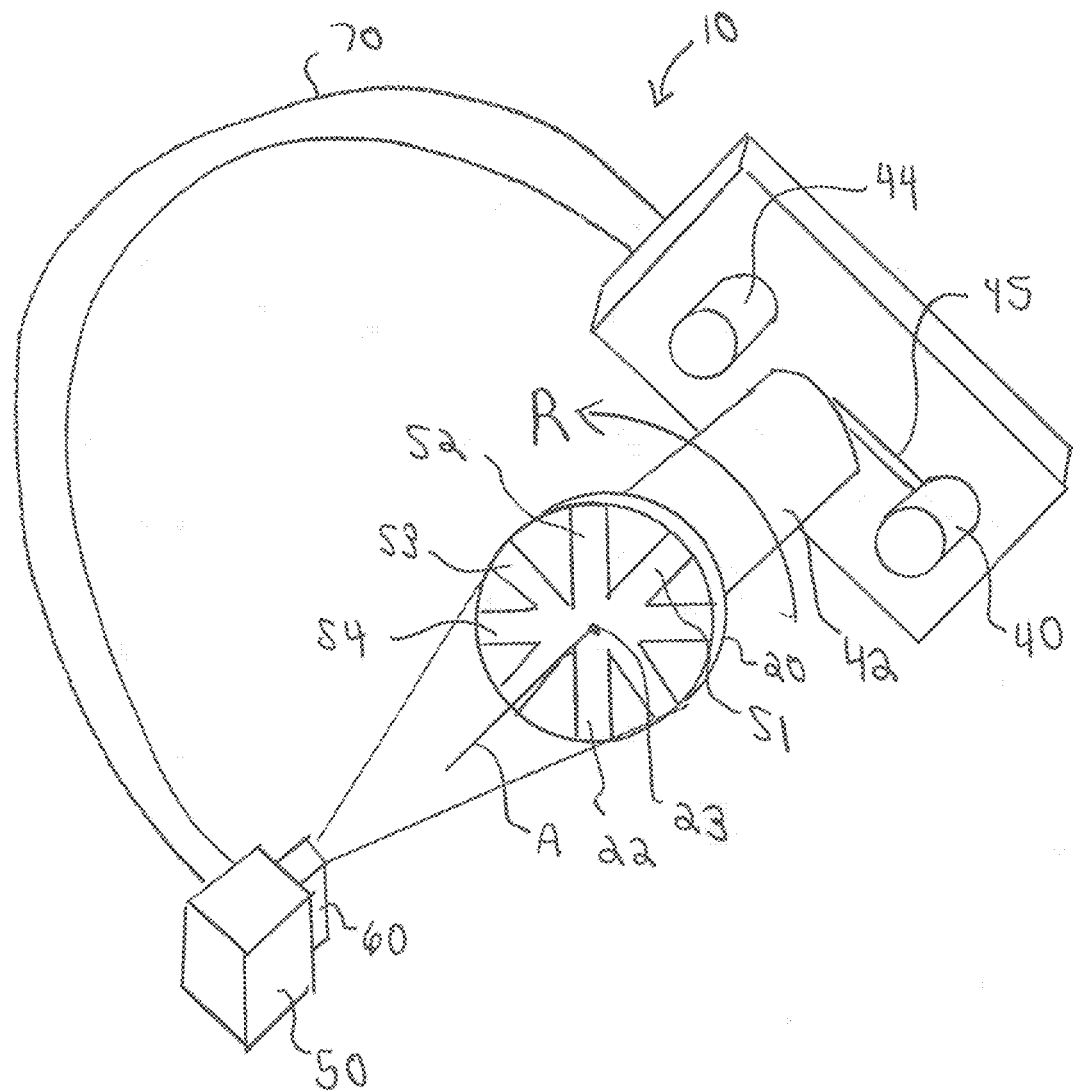
FIG. 1 is a schematic perspective view of the present system in operation.

FIG. 1 shows a schematic view of the present system in operation, as follows. The present system 10 comprises a rotatable plate 20, a drive assembly 40 for rotating plate 20, an X-ray generator 50, a beam collimator 60, and a C-arm 70 connecting X-ray generator 50 to an assembly 25 comprising rotatable plate 20 and drive assembly 40. In operation, an object O (see FIG. 4) is placed between X-ray generator 50 and rotatable plate 20.

Figure 2:
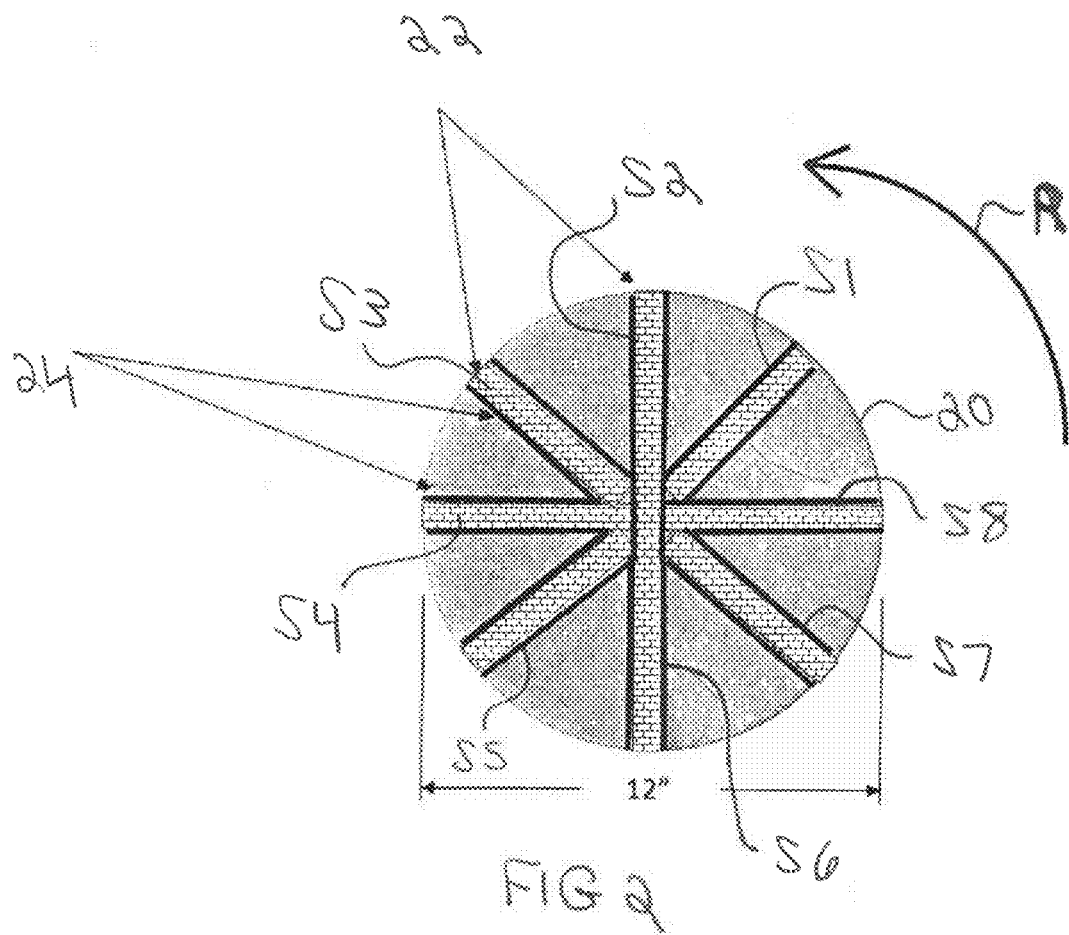
FIG. 2 is a front elevation view of the rotatable plate, showing the spokes of detectors thereon.

As best seen in FIG. 2, rotatable plate 20 comprises a plurality of radiographic image detectors 22 disposed thereon. Most preferably, the plurality of radiographic image detectors 22 are arranged as spokes (S1, S2, etc.) extending radially outwardly from a central rotational point 23 on rotatable plate 20. Drive assembly 40 is configured to rotate rotatable plate 20 around an axis A extending through central rotational point 23. It is to be understood, however, that the present system also encompasses the embodiment where only a single spoke is used, and is rotated around in a circular path (appearing similar to one hand moving on a clock).

It is to be understood that different numbers of spokes S1 to $S_n$, can be used. As will be explained, the exact number of spokes used will correspond to the desired number of image frames to be taken per second, and to the speed at which rotatable plate 20 is rotated. As such, the numbers of spokes S1 to $S_n$ can be an even number or an odd number, or even a single spoke. However, in the one illustrated embodiment, the plurality of radiographic image detectors 22 are arranged as eight spokes (S1 to S8), positioned at 45 degree angles to one another, as shown.

In operation, rotatable plate 20 is rotated (in direction R) at a speed such that the duration of each image frame corresponds to the time taken for each spoke of the plurality of radiographic image detectors 22 to move to the position of an adjacent spoke of the plurality of radiographic image detectors 22. For example, each image frame will last for a duration of time sufficient for the plurality of radiographic image detectors 22 on spoke S1 to move to the position of spoke S2 (which is the same as the duration of time sufficient for the plurality of radiographic image detectors 22 on spoke S2 to move the to the position of spoke S3, etc.) As such, the present system 10 will capture a full "swept image" of the object O. Stated another way, rotatable plate 20 is rotated at a speed such that the duration of successive image frames corresponds to the time taken for each spoke S of the plurality of radiographic image detectors 22 to move to the position of an adjacent spoke of the plurality of radiographic image detectors 22. In the exemplary embodiment of FIG. 2, rotatable plate 20 is rotated at 3 rotations per second, thus resulting in 24 image frames per second being taken. In this particular embodiment, the diameter of rotatable plate 20 is 12 inches, but it is to be understood that other dimensions can be used instead.

The advantage of the present system 10 is that it avoids the problem of off-axis X-ray beam scattering (which would otherwise produce foggy resulting images). Instead, images are basically taken "on-axis" with the present system 10, but with the axis of the image being rotated during each image frame to produce much clearer images.

Preferably as well, rotatable plate 20 also has collimators 24 disposed thereon. Preferably, collimators 24 are positioned on the side edges of spokes S1 to S8, as shown. Collimators 24 are preferably raised up (several millimeters or centimeters) from the surface of rotatable plate 20 and may optionally comprise strips of lead (or other X-ray absorbing material). Collimators 24 function to prevent scattering of the X-rays, thereby stopping scattered radiation from illuminating detectors 22.

In operation, an object 0 (FIG. 4) is positioned between X-ray generator 50 and a rotatable plate 20. Optionally, this object O can be a horse, or any other large animal, or a person, or conceivably any other object. X-ray generator 50 is positioned to emit an X-ray beam across the surface of rotatable plate 20. As also best seen in FIG. 4, the center of beam B is preferably collinear with the axis A extending through the central rotational point 23 of rotatable plate 20.

Optionally, a beam collimator 60 is positioned between X-ray generator 50 and rotatable plate 20. Beam collimator 60 is preferably configured to emit a conical shaped beam B that is centered on axis A. In another embodiment (e.g.: where only one spoke is used), the beam collimator 60 can be used to flatten the beam B such that the beam B is a fan-shaped slit that is incident on the single spoke. In this embodiment, the flattened beam B can be rotated together with the rotatable plate 20 such that the beam B remains incident on the spoke. One advantage of using such a flattened beam B is that dosage is reduced, which is desirable both for the patient and the veterinarian present in the room. C-arm 70 connects the assembly 25 housing drive assembly 40 and the X-ray generator 50.

To produce a swept image, the pixels of the radiographic image detector 22 are preferably smaller towards the center of the rotatable plate 20 (central rotational point 23) and larger towards the outer perimeter of rotatable plate 20. This is due to the fact that the pixels of the radiographic image detector 22 that are closer to the outer perimeter of rotatable plate 20 are required to travel a greater physical distance during frame-to-frame rotation. Stated another way, the detector pixel density is preferably higher towards the central rotational point 23 of rotatable plate 20 and smaller towards the outer perimeter of rotatable plate 20. In constructing an embodiment of the present system 10, the present inventors used 3-inch spokes S1 to S8. The outermost segments had a pixel pitch of 1.6 mm and the innermost segments had a pixel pitch of 0.2, 0.4, 0.8 or 0.16 mm. Using smaller pixels on the innermost segments helped to offset the disparity of the relative speed and distance covered between the innermost and outermost segments as the rotatable plate 20 rotates. It is to be understood, however, that different arrangements of radiographic image detectors 22 can be used.

Figure 3:
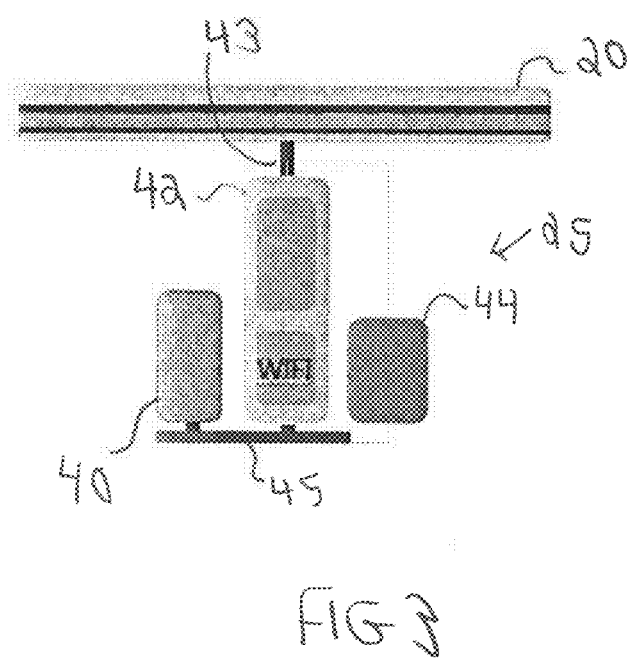
FIG. 3 is a top perspective view of the rotatable plate, drive motor and power supply.

FIG. 3 illustrates further details of assembly 25 which includes drive assembly 40 (for rotating plate 20), camera electronics 42 and a power supply 44. An image processing computer and display system (not shown) is preferably also included to provide an interface to control the operation of X-ray generator 50, to display acquired images and to archive images and store associated patient information. FIG. 3 also shows a shaft 43 passing through camera electronics 42. A system of gears 45 between drive assembly 40 and shaft 43 causes drive assembly 40 to rotate rotatable plate 20. The camera data is preferably transmitted to the electronics 42 by wifi.

The present system 10 also provides a method of obtaining a fluoroscopic image, by: (a) positioning an object O between an X-ray generator 50 and a rotatable plate 20 having a plurality of radiographic image detectors 22 thereon, wherein the plurality of radiographic image detectors 22 are arranged as one or more spokes S1 to Sn extending radially outwardly from a central rotational point 23 on the rotatable plate 20; (b) directing an X-ray beam B through the object O towards the plurality of radiographic image detectors 22 on the rotatable plate 20; while (c) rotating the rotatable plate 20, such that the plurality of radiographic image detectors 22 on the rotatable plate 20 obtain a swept image of portions of the object O between the adjacent spokes of radiographic image detectors 22. As the rotatable plate 20 rotates, the plurality of radiographic image detectors 22 sweep over a circular area to produce an X-ray image of the area.

Lastly, a Graphical User Interface (GUI) installed on a pc workstation to provide a control interface to control the x-ray generator 50 and the fluoroscope, display acquired images as well as image processing functions, image archiving and entering patient demographics.

What is claimed is:

1. A fluoroscopic imaging system, comprising: (a) a rotatable plate; (b) one or more detectors disposed on the rotatable plate, wherein the one or more detectors are arranged as one or more spokes extending radially outwardly from a central rotational point on the rotatable plate; and (c) a drive assembly configured to rotate the rotatable plate about an axis extending through the central rotational point, and (d) collimators disposed on side edges of the one or more spokes.

2. The fluoroscopic imaging system of claim 1, wherein the collimators comprise strips of lead.

3. The fluoroscopic imaging system of claim 1, further comprising: (d) an X-ray generator positioned to emit an X-ray beam across a surface of the rotatable plate.

4. The fluoroscopic imaging system of claim 3, wherein a center of the X-ray beam is collinear with the axis extending through the central rotational point of the rotatable plate.

5. The fluoroscopic imaging system of claim 3, further comprising: (e) a beam collimator positioned between the X-ray generator and the rotatable plate, wherein the beam collimator is configured to emit a conical beam centered on the axis extending through the central rotational point of the rotatable plate.

6. The fluoroscopic imaging system of claim 3, further comprising: (e) a beam collimator positioned between the X-ray generator and the rotatable plate, wherein the beam collimator is configured to emit a flattened fan-shaped planar beam that is incident on the one or more detectors on the rotatable plate.

7. The fluoroscopic imaging system of claim 3, further comprising: (e) a C-arm connecting the drive assembly to the X-ray generator.

8. The fluoroscopic imaging system of claim 1, wherein the one or more detectors comprise detector pixels, wherein the detector pixels are smaller towards the central rotational point of the rotatable plate and larger towards an outer perimeter of the rotatable plate.

9. The fluoroscopic imaging system of claim 1, wherein the one or more detectors comprise detector pixels, wherein a density of the detector pixels is higher towards the central rotation point of the rotatable plate and smaller towards an outer perimeter of the rotatable plate.

10. A fluoroscopic imaging system, comprising: (a) a rotatable plate; (b) one or more detectors disposed on the rotatable plate, wherein the one or more detectors are arranged as one or more spokes extending radially outwardly from a central rotational point on the rotatable plate; and (c) a drive assembly configured to rotate the rotatable plate about an axis extending through the central rotational point, wherein the one or more detectors are arranged as 8 spokes, positioned at 45 degree angles to one another.

11. A method of obtaining a fluoroscopic image, comprising: (a) positioning an object between an X-ray generator and a rotatable plate having a plurality of detectors thereon, wherein the plurality of detectors are arranged as spokes extending radially outwardly from a central rotational point on the rotatable plate; (b) directing an X-ray beam through the object towards the plurality of detectors on the rotatable plate; while (c) rotating the rotatable plate, such that the plurality of detectors on the rotatable plate obtain a swept image of portions of the object between adjacent spokes of detectors, and (d) using a beam collimator to emit a conical beam centered on an axis extending through the central rotational point of the rotatable plate.

12. The method of claim 11, wherein directing an X-ray beam through the object towards the plurality of detectors on the rotatable plate comprises taking successive image frames, and wherein a duration of each image frame corresponds to a time taken for each spoke of detectors to move to a position of an adjacent spoke of detectors.

13. The method of claim 11, wherein rotating the rotatable plate comprises rotating the rotatable plate at a speed such that a duration of successive image frames corresponds to a time taken for each spoke of detectors to move to a position of an adjacent spoke of detectors.

14. The method of claim 11, wherein there are 8 spokes of detectors, and wherein rotating the rotatable plate comprises rotating the rotatable plate at 3 rotations per second.

15. The method of claim 11, wherein the object is a large animal.

16. The method of claim 15, wherein the large animal is a horse.

17. The method of claim 11, further comprising: (d) using a beam collimator to emit a flattened fan-shaped planar beam incident on the plurality of detectors on the rotatable plate.

* * * * *